(12) United States Patent
Shoesmith

(10) Patent No.: US 9,260,785 B2
(45) Date of Patent: Feb. 16, 2016

(54) INSPECTION OF A COMPONENT

(75) Inventor: John P. Shoesmith, Derby (GB)

(73) Assignee: ROLLS-ROYCE plc, London (GB)

( * ) Notice: Subject to any disclaimer, the term of this patent is extended or adjusted under 35 U.S.C. 154(b) by 818 days.

(21) Appl. No.: 13/524,806

(22) Filed: Jun. 15, 2012

(65) Prior Publication Data

US 2013/0002850 A1    Jan. 3, 2013

(30) Foreign Application Priority Data

Jun. 29, 2011 (GB) .................................. 1111039.2

(51) Int. Cl.
*H04N 7/18*     (2006.01)
*C23C 26/02*    (2006.01)
*G01N 21/84*    (2006.01)

(52) U.S. Cl.
CPC ........ C23C 26/02 (2013.01); *G01N 2021/8427* (2013.01)

(58) Field of Classification Search
CPC ......................... C23C 26/02; G01N 2021/8427
USPC .......................................................... 348/87
See application file for complete search history.

(56) References Cited

U.S. PATENT DOCUMENTS

| | | | |
|---|---|---|---|
| 3,224,084 A * | 12/1965 | Russell | B21D 51/00 138/154 |
| 3,681,970 A | 8/1972 | Wells | |
| 4,934,813 A | 6/1990 | Yaginuma et al. | |
| 2003/0048496 A1* | 3/2003 | Laming | G02F 1/011 398/164 |
| 2004/0196453 A1 | 10/2004 | Some | |
| 2010/0008462 A1 | 1/2010 | Killian et al. | |

FOREIGN PATENT DOCUMENTS

| | | |
|---|---|---|
| DE | 10202792 A1 | 8/2003 |
| DE | 102010018980 A1 | 11/2011 |
| JP | 61-132848 | 6/1986 |
| JP | 61-193055 | 8/1986 |
| JP | 10-10280 | 1/1998 |

OTHER PUBLICATIONS

Nov. 8, 2012 European Search Report issued in European Application No. 12172204.

Sep. 26, 2011 Search Report issued in British Patent Application No. 1111039.2.

* cited by examiner

*Primary Examiner* — Yulin Sun

(74) *Attorney, Agent, or Firm* — Oliff PLC

(57) ABSTRACT

A component such as a pressure vessel includes a cladding layer bonded to a substrate by a welding process. The component is inspected by a method that includes using a first camera to record a first image of an inspection portion of the cladding layer, the inspection portion having a pattern of markings; causing or allowing a temperature change in the component; using a second camera to record a second image of the inspection portion; and identifying the deformation of the pattern of markings on the inspection portion by reference to relative movement of the respective markings between the first and second image. The temperature change may occur as a result of cooling of the component after the welding process. Analysis of the deformation may be conducted by a Digital Image Correlation process, enabling possible defects or flaws in the component to be identified.

15 Claims, 4 Drawing Sheets

INSPECTION OF A COMPONENT

This invention relates to a method and apparatus for inspecting a component comprising a cladding layer bonded to a substrate.

A cladding layer, or clad, may be bonded to a base material of a component to provide a desirable property to the surface of the component. For example, a pressure vessel may be constructed of carbon steel alloys for strength, and then be provided on its internal surface with a layer of corrosion resistant material such as stainless steel.

Many methods for bonding a cladding layer to the base material of a substrate are known in the art. Welding methods such as GMAW (Gas Metal Arc Weld), SAW (Submerged Arc Welding) and ESC (Electro Slag Cladding) form a molten pool penetrating the original surface of the base material, the molten pool comprising molten electrode, strip or wire material and base material. The molten pool solidifies to form a weld bead, thereby providing the cladding layer. Laser welding and Laser-hybrid welding (e.g. Laser welding with GMAW welding) can also be used to provide a cladding layer. Solid state bonding processes such as FSW (Friction Stir Welding) form a bond between the base material and a cladding layer at temperatures lower than the melting point of either material by plastically deforming and fusing the two materials by a physical bond. There are also other forms of solid state bonding. For example, DFW (Diffusion Welding, also known as Diffusion Bonding), uses high temperature and pressure to join metals, which may be dissimilar. Solid state bonding is a process where no cast product is formed.

Imperfections and defects can arise in the bond between a cladding layer and a base material, such as inclusions, liquation cracking and lack of fusion.

Liquation cracking can occur in a weld bead or the base material due to localised thermal strains associated with the bonding process. Cracks can appear at the toe of a weld where there is poor fusion with the base material. In some cases the crack width can be extremely narrow and hard to detect.

A lack of fusion can arise between the base material and the cladding layer, or between successive cladding layers in a multi-run cladding process.

A lack of fusion can arise if the base material is not melted enough during welding. Rather than the two metals coalescing to form a weld bead, a bond is formed between the molten electrode and the solid base material, similar to that formed by brazing.

Inter-run defects can occur in multi-layer welds between the layers or between adjacent weld beads if oxides or slag are allowed to form on the surface of the previous weld bead. The oxides or slag have a higher melting point than the weld bead, which can result in a lack of fusion between the beads because the previous weld bead is prevented from melting and coalescing with the new weld bead to form a strong bond.

Solid state bonding processes can also suffer from a low strength or non-continuous bond when the base material and cladding layer are not able to fuse together owing to low temperatures or imperfections.

Where the surfaces of the base material and cladding layer are in contact, but a strong atomic bond has not been formed over the full contact area, this is referred to as a "kissing bond". Kissing bonds can result from the lack of fusion defects described above for both welding and solid state bonding processes.

Each of the above mentioned defects results in a reduced strength bond between the base material and the cladding layer, and so it is desirable to inspect the interface between the base material and the cladding layer for defects. However, some of these defect types, e.g. kissing bonds, are either difficult or impossible to detect using known inspection methods.

Further, inspection methods such as radiographic or ultrasonic inspection are expensive and time-consuming to perform since they require specialist equipment and can only analyse a small portion of a component at any one time. Ultrasonic inspection is slow since the probe must be accurately positioned and moved slowly over the surface. The surface must be prepared for inspection so that it is smooth, relatively cool and clean. Radiographic inspection usually takes place in a specific inspection area remote from the manufacturing area to protect workers from X-ray exposure.

Once a defect is detected in a completely clad component using these techniques, it can be expensive to repair and re-inspect the defect as the materials used are difficult to grind or machine.

Where there are multiple cladding layers, intermediate inspection and repair is often undertaken to minimise later remedial repairs, which is costly and time consuming.

According to a first aspect of the invention there is provided a method for inspecting a component comprising a cladding layer bonded to a substrate, the method comprising the steps of: recording a first image of an inspection portion of the cladding layer, the inspection portion having a pattern of markings; causing or allowing a temperature change in the component; recording a second image of the inspection portion; and identifying the deformation of the pattern of markings on the inspection portion by reference to relative movement of the respective markings between the first and second images.

The deformation of the pattern of markings on the inspection portion may be identified by DIC (Digital Image Correlation).

The cladding layer and the substrate may have different coefficients of thermal expansion.

The method may further comprise the step of identifying regions of anomalous deformation of the pattern on the inspection portion to identify the locations of possible flaws in the component, for example in the bond between the cladding layer and the substrate.

The pattern of markings may be formed by a cladding process used to bond the cladding layer to the substrate.

The inspection portion, and in particular the exposed surface of the cladding layer, may have inherent markings which are sufficiently discernible in the first and second images to enable the deformation to be identified. However, in some embodiments, the method may further comprise the step of applying the markings to the inspection portion.

According to a second aspect of the invention, there is provided a method for manufacturing a component comprising the steps of: applying a cladding layer to a substrate by a cladding process, thereby forming the component; and inspecting the component by a method according to the first aspect of the invention.

The cladding process may cause heating of the component to an elevated temperature, the temperature change occurring as a result of cooling of the component from the elevated temperature.

The component may be heated to the elevated temperature by heating means independently of the cladding process, the temperature change occurring as a result of the temperature elevation to and/or the subsequent cooling of the component from the elevated temperature.

The cooling of the component may be effected by cooling means. The cooling of the component may be determined by the ambient environment.

The cladding process and the inspection steps may be applied concurrently to adjacent portions of the component.

The cladding process and the inspection steps may be performed respectively by cladding equipment and inspection equipment. There may be relative movement between the component and the cladding and inspection equipment. The inspection equipment may be situated after the cladding equipment with respect to the direction of movement of the component. The inspection equipment may comprise first and second cameras which record the first and second images, respectively. A portion of the component at which the cladding layer has been applied by the cladding equipment may pass the first camera and subsequently pass the second camera.

Marking equipment for applying the markings to the inspection portion may be located between the cladding equipment and the first camera.

Either or both of the heating and cooling apparatuses for heating and cooling the inspection portion may be located between the first and second cameras.

The relative movement may be rotational movement about a rotational axis, the component comprising a substantially cylindrical or other body shape with rotational symmetry.

There may be relative axial movement between the component and the cladding and inspection equipment with respect to the body, such that the cladding layer may be formed in a helix on the component.

The cladding process may be a welding process, a diffusion bonding process or a friction welding process.

According to a third aspect of the invention there is provided inspection equipment for performing an inspecting method in accordance with the first aspect of the invention, the equipment comprising: a first camera arranged to record a first image of an inspection portion of the cladding layer; a second camera spaced from the first camera and arranged to record a second image of the inspection portion; drive means for causing relative displacement between the inspection equipment and the component so as to displace the inspection portion in a displacement direction from the first camera to the second camera; and processing means for identifying the deformation of a pattern of markings on the inspection portion by reference to relative movement of the respective markings between the first and second images.

The inspection equipment may further comprise marking equipment for applying markings to the inspection portion, the marking equipment being disposed ahead of the first camera with respect to the displacement direction.

The inspection equipment may further comprise heating means for heating the component to an elevated temperature.

The inspection equipment may further comprise cooling means disposed after the heating means and/or the first camera, and ahead of the second camera, with respect to the displacement direction.

According to a fourth aspect of the invention there is provided apparatus for manufacturing a component comprising a substrate provided with a cladding layer, the apparatus comprising cladding equipment for applying the cladding layer to the substrate, and inspection equipment in accordance with the third aspect of the invention, wherein the cladding equipment is disposed ahead of the first camera with respect to the displacement direction.

In embodiments in which the inspection equipment of the apparatus comprises heating means for heating the component to an elevated temperature, the heating means may be the cladding equipment. For example, the cladding equipment may heat up the component to such a temperature as part of the cladding process that no further heating is required to effect a suitable temperature change between the recording of the first and second images by the first and second cameras respectively.

With reference to any method, inspection equipment or apparatus in accordance with the invention, the component may be a pressure vessel and the cladding layer may be applied to an internal surface of the pressure vessel.

With reference to any method, inspection equipment or apparatus in accordance with the invention, the component may be a fuel plate and the cladding layer may be applied to an external surface of the fuel plate.

The invention may comprise any combination of the features and/or limitations referred to herein, except combinations of such features as are mutually exclusive.

A method, inspection equipment or apparatus in accordance with the invention allows the component to be inspected quickly and relatively economically to detect the locations of possible imperfections in the clad such as sub-surface cracks, inclusions, poor bonding or lack of fusion. Other inspection techniques may then be used to inspect the portion in more detail.

A method, inspection equipment or apparatus in accordance with the invention enables the component to be inspected concurrently with the cladding process at adjacent portions of the component, thereby eliminating the need for entirely separate cladding and inspection processes. The invention therefore allows remedial action to be taken at the earliest possible opportunity to reduce the cost and time of manufacture.

An inspection method or equipment in accordance with the first and third aspects of the invention may also be applied independently of a cladding process, for example, for in-service inspection.

In contrast with previously considered inspection methods, a method, inspection equipment or apparatus in accordance with the invention examines the effect of the defect, rather than attempting to detect its form or composition. Previously considered methods have difficulty in detecting certain defects because their physical form is difficult or impossible to discern. For example there is no discernible crack or gap at kissing bonds, although a strong bond has not been formed between the adjacent materials.

For a better understanding of the invention, and to show how it may be carried into effect, reference will now be made, by way of example, to the accompanying drawings, in which.

A method, inspection equipment and apparatus in accordance with the invention are described with reference to a component in the form of a pressure vessel 2 depicted in FIG. 1.

The vessel 2 has a cylindrical body 10 of approximately 3 m in diameter, however, the skilled person will appreciate that other diameter bodies may be used. The central axis 12 of the body 10 is horizontal, and the vessel 2 sits on a pair of rollers 14. At least one of the rollers 14 is driven in order to rotate the pressure vessel around its central axis 12 in a clockwise direction. The rollers 14 are in communication with a rotation control system (not shown) for controlling the rotation of the pressure vessel. The body 10 is made of carbon steel which has good tensile properties.

Figure 1:
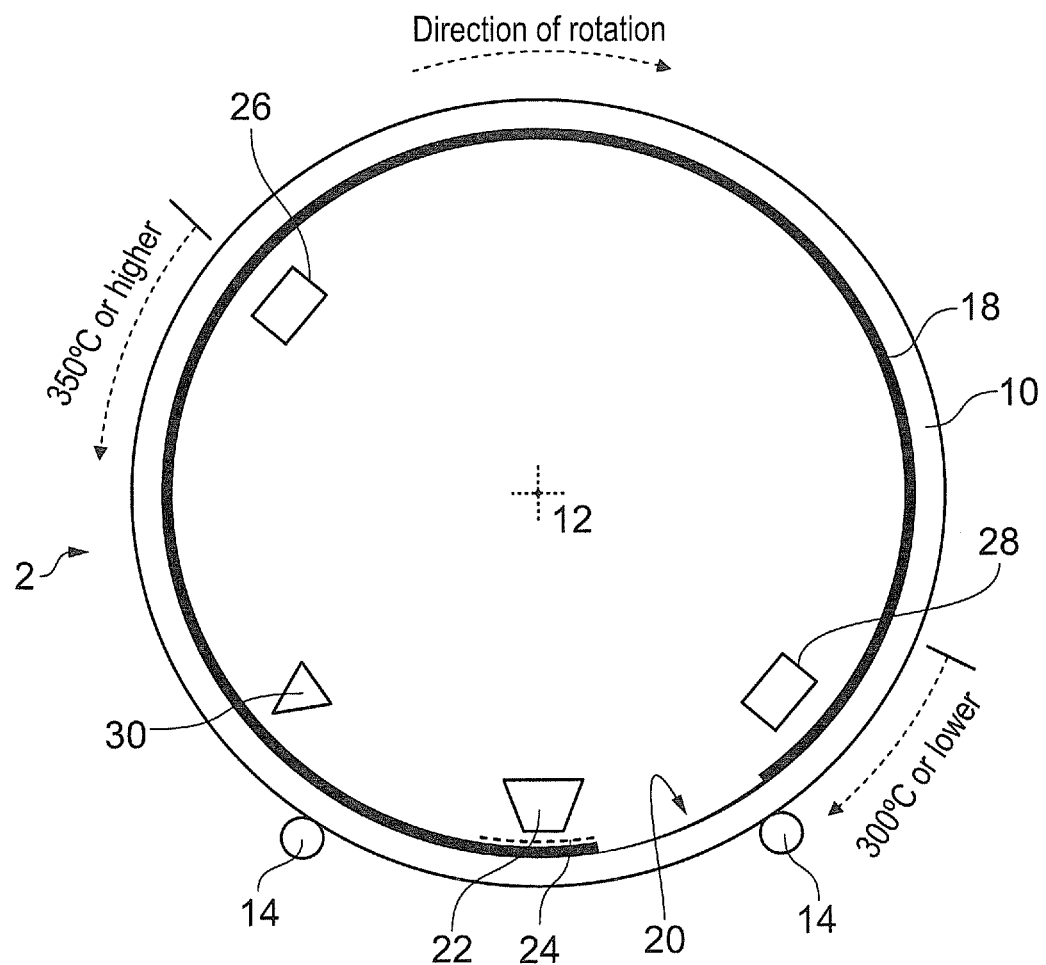
FIG. 1 shows in schematic sectional view a pressure vessel with cladding and inspection equipment in accordance with the invention.

FIG. 1 shows a stainless steel cladding layer 18 being applied to the internal surface 20 of the body 10 by cladding equipment 22.

The cladding equipment 22 comprises a welding head suitable for ESCW (Electro Slag Cladding), although it will be appreciated that any alternative welding or bonding process may be used. The cladding equipment 22 depicted in FIG. 1 is adjacent to the internal surface 20 of the body 10 at the appropriate position, which, in this embodiment is towards the 6 o'clock position as viewed in FIG. 1. The skilled person will appreciate that the cladding equipment may be offset by a few degrees, for example, six degrees, to one side. The portion of the internal surface 20 of the body 10 opposite the cladding equipment 22 is referred to as the cladding zone 24.

FIG. 1 also shows inspection equipment comprising first and second cameras 26, 28 situated within the body 10, generally diametrically opposite each other. In the embodiment shown, the first camera 26 and the second camera 28 are located at approximately 10 o'clock and 4 o'clock positions respectively. A clean up unit in the form of a slag removal device 30, which may be a wire brush, is located at approximately the 7 o'clock position.

The cladding and inspection equipment 22, 26, 28 is mounted on a manipulator (not shown) for positioning the cladding and inspection equipment 22, 26, 28 with respect to the body 10. The equipment is displaceable by the manipulator in a direction parallel to the rotational axis 12 of the body 10, but is stationary about the axis 12.

Drive to the rollers 14 and to the manipulator carrying the equipment 22, 26, 28 and the slag removal device 30 is controlled by a computer (not shown) so as to cause rotation of the body 10 and axial movement of the cladding and inspection equipment 22, 26, 28, such that the cladding layer 18 is welded to the internal surface 20 of the body 10 in a helix formation.

Figure 2:
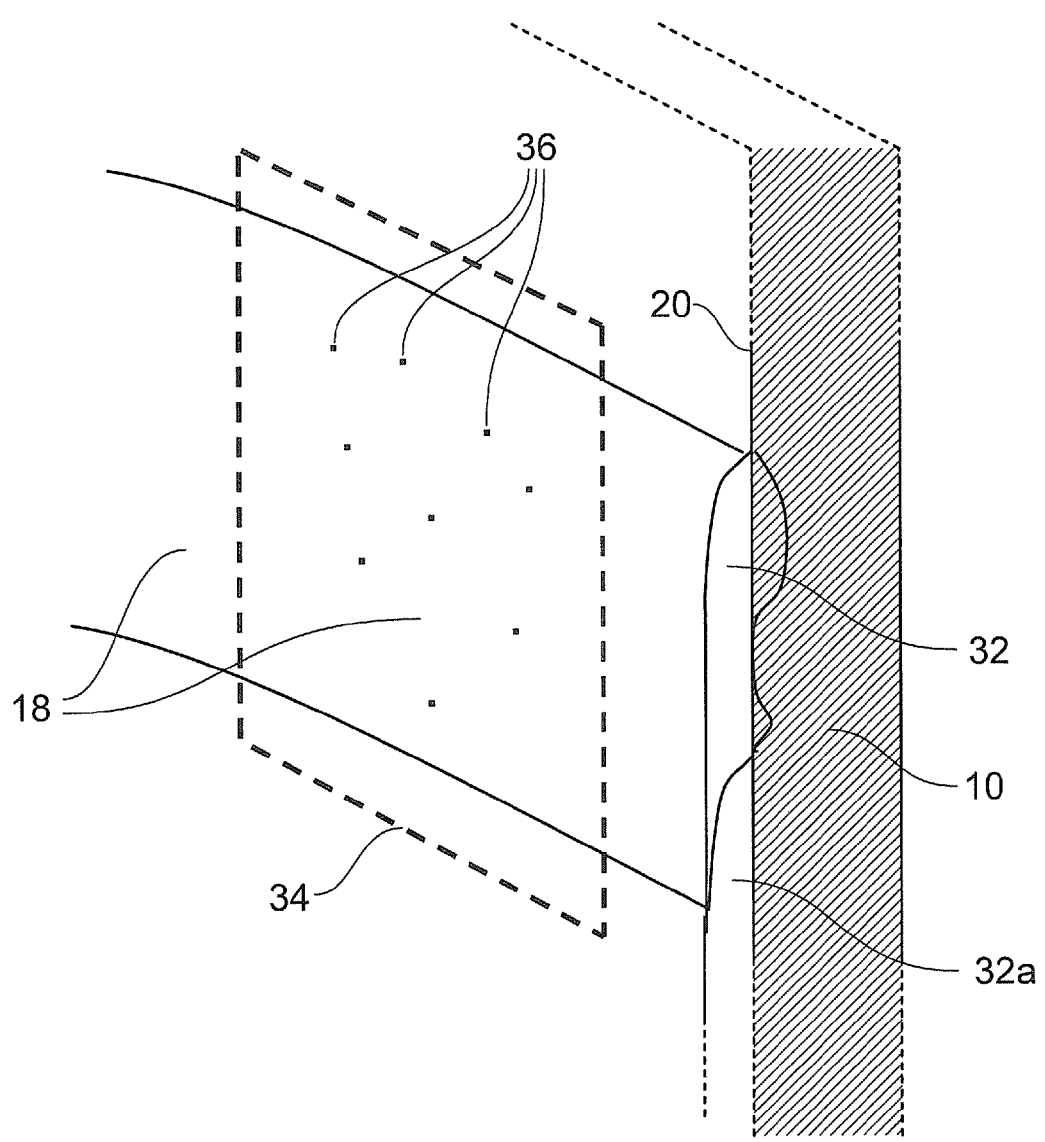
FIG. 2 shows an inspection portion of the cladding layer formed on the internal wall of the pressure vessel of FIG. 1.
Figure 3:
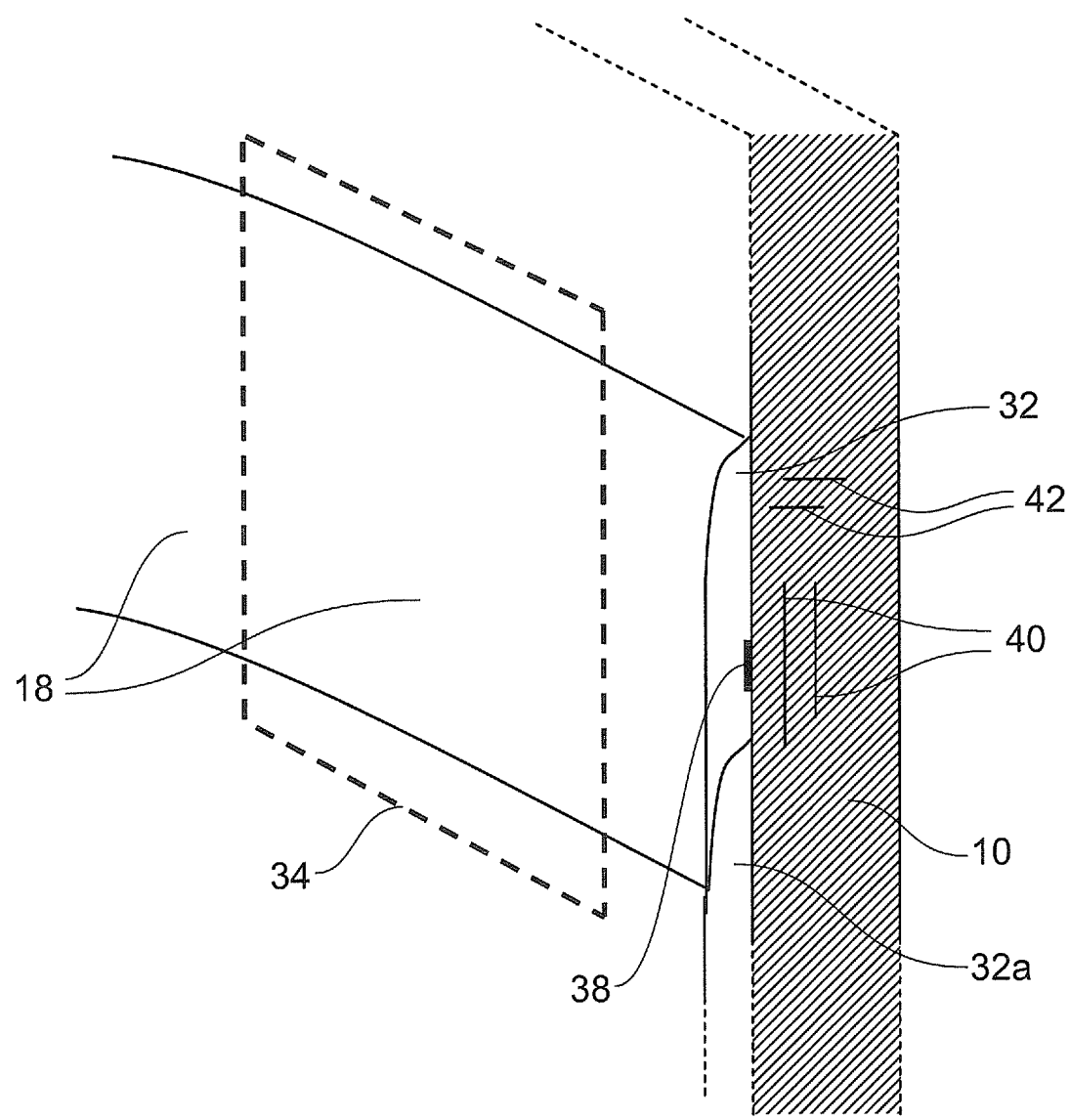
FIG. 3 shows exemplary defects that may form near the interface of the cladding layer and pressure vessel of FIG. 1.

In this example embodiment, the cladding process is ESC (Electro Slag Cladding). The cladding equipment 22 comprises a welding head (not shown) which feeds a consumable stainless steel electrode in the form of a strip to the cladding zone 24. An electric current is conducted through the electrode into the slag formed at the weld zone. The slag heats up due to ohmic resistance, thereby melting the adjacent part of the electrode and a portion of the internal wall 20 of the pressure vessel 2 to form the weld bead 32 as shown in FIGS. 2 and 3. A weld bead portion 32a from a previous helical pass is also shown.

The welding process generates substantial heat and consequently the weld bead 32 and the substrate constituted by the local region of the body 10 are at an elevated temperature on leaving the cladding zone 24. As the body 10 rotates and the weld bead 32 moves further from the cladding zone 24, the temperature falls as a result of cooling by the ambient air.

The solidified slag formed on the top of the weld bead 32 is removed by the slag removal device 30, exposing the surface of the weld bead 32. The surface of the weld bead 32 is not perfectly smooth, but exhibits roughness and surface defects which constitute a pattern of markings 36 (FIG. 2).

The first camera 26 records a succession of images of the weld bead 32. Each image can be regarded as an image of an inspection portion 34 and the markings 36 on it. Having cooled from the elevated temperature at the cladding zone 24, each inspection portion 34 when imaged by the first camera 26 may, for example, be at 350° C.

Each inspection portion 34, i.e. each recorded image, extends over the full axial width of the weld bead 32, with reference to the axis 12, and successive inspection portions may abut or overlap one another. Consequently, the first camera 26 records images which, together, show the entire weld bead 32.

Each inspection portion 34 continues to cool as the body 10 is rotated. On arrival at the second camera 28, the temperature of the inspection portion 34 may be approximately 300° C. The second camera 28 records a second image of the inspection portion 34 and markings 36. The second image of each inspection portion 34 is registered with the first by any suitable means, for example by reference to the displacement of the body 10 and the cladding and inspection equipment 22, 26, 28, or by providing registration markings on the surface of the weld bead 32.

Each inspection portion 34 thus undergoes a temperature change as it moves from the first camera 26 to the second camera 28. The temperature change gives rise to thermal stresses and thermal strains in both the body 10 and the cladding layer 18 local to the inspection portion 34.

The coefficients of thermal expansion of the carbon steel body 10 and the stainless steel cladding layer 18 are different. Nevertheless, if the cladding layer 18 is fully bonded to the substrate material of the body 10 without defects, the cladding layer 18 will be constrained to move with the body 10 as the temperature reduces. The body 10 is generally of uniform thickness and composition, and so it should respond to the temperature change with a uniform, regular, or readily predictable pattern of thermal strain.

However, defects in the bond between the cladding layer 18 and body 10, or between adjacent passes of the weld bead 32, 32a could allow the strain response of the cladding layer 18 to the temperature change to be less constrained by the deflection of the underlying pressure vessel 2 in the region of a defect. This could result in an anomalous pattern of deformation at the outer surface of the cladding layer 18 in response to the temperature change. By "anomalous" in this context it is meant that the deformation that occurs is different from the deformation expected when the cladding layer 18 is fully bonded to the substrate material of the body 10.

Example defects 38, 40, 42 are shown in FIG. 3. FIG. 3 shows a lack of fusion defect, or kissing bond defect, 38; and vertically and horizontally oriented cracks 40, 42 in the material of the body 10. Other defects may be inclusions in the weld bead and a lack of fusion between the weld beads which may be between two adjacent weld beads in an axial or radial direction.

The pattern of deformation of the outer surface of the cladding layer 18 in response to the temperature change is identified by tracking the relative movement of the respective markings 36 on the inspection portion 34 between the first and second images.

Suitable software is used to analyse the movement of markings 36 between the first and second images using DIC (Digital Image Correlation).

Figure 4:
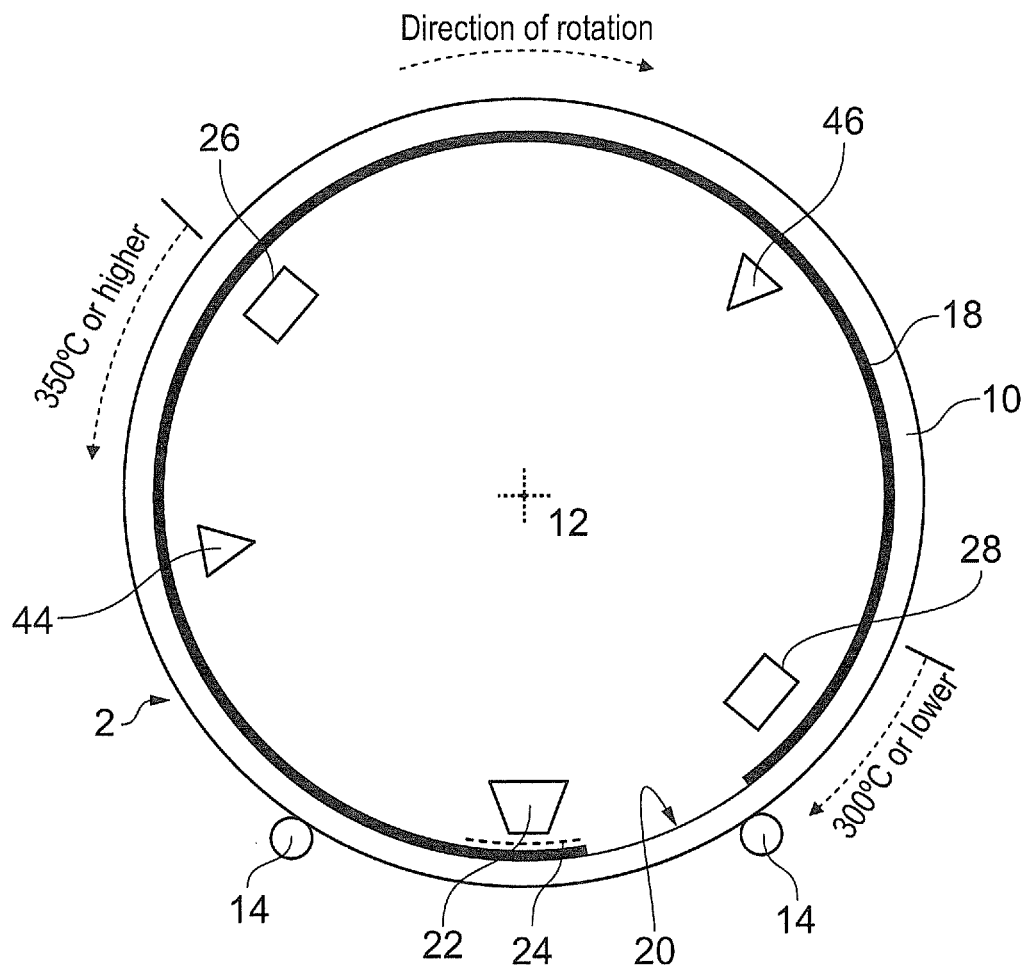
FIG. 4 shows in schematic sectional view a pressure vessel with cladding and inspection equipment in accordance with alternative embodiments of the invention.

Thus, the first image is analysed by means of software and at least three of the markings 36 are identified and their positions relative to each other are recorded. The markings may be the result of surface imperfections left on the surface of the weld bead 32 after slag removal, or they may be formed deliberately on the weld bead 32 by a suitable marking device 44 (FIG. 4).

The second image is registered with the first image and is also analysed to identify the same markings 36 and their relative positions. As a result of the thermal strain caused by the temperature change between the two images, the relative positions of the markings 36 in the second image will differ by comparison with the first image. This difference is processed by the software to produce an output representing the strain that has occurred at the surface of the weld bead 32.

In regions where the weld bead 32 is fully bonded to the body 10, the strain output will be relatively uniform over the inspection portion 34. However, if a region of the weld bead 32 is not fully bonded, the strain response output of the weld bead 32 will be different from that of a fully bonded region of the weld bead 32, and this region will be registered by the software as a region of anomalous deformation.

For example, the DIC method may produce a contour plot of strain throughout the inspection portion 34. This contour plot may have regions of local anomalous strain, which would be identified as locations of possible defects in the bond between the body 10 and the cladding layer 18.

The or each anomalous region can then be investigated further by other techniques in order to confirm the existence of a defect, and to diagnose its nature. Suitable remedial action can then be taken.

Since the rotation of the pressure vessel 2 and the axial movement of the cladding and inspection equipment 22, 26, 28 are under computer control, the position of any anomalous region can be recorded accurately for subsequent investigation and repair. Alternatively, registration of the images may be achieved by recognition of defects or deliberate surface markings on the surface of the cladding layer 18.

Alternative embodiments of the invention may differ in that the cladding process may not produce slag. Such embodiments would not require a slag removal device 30 and/or a method step for removing slag.

In some circumstances, enhanced cooling of the body 10 and cladding layer 18 may be required in order to increase the temperature change between the first and second cameras 26, 28. For this purpose a cooling device 46 (FIG. 4) may be positioned between the cameras 26, 28 to provide active cooling of the cladding layer 18 and pressure vessel 2. The cooling device 46 may be a blower directing ambient air at the cladding layer 18, or may incorporate a refrigeration unit.

Alternatively, or in addition, supplementary heating of the cladding layer 18 may be achieved by a heating device. For example, a laser may be located before the first camera 26, thereby enabling a larger temperature drop between the first and second cameras. The laser may be controlled to emit pulses of energy, or a continuous line. Supplementary heating as described may be particularly useful when low-temperature cladding processes are employed, such as diffusion welding or diffusion bonding In the process described above, the temperature change between the first and second cameras 26, 28 has resulted from the cooling of the cladding layer 18. Alternatively, the temperature change could be an increase. For example, supplementary heating of the cladding layer 18 may be provided between the first and second cameras 26, 28.

Any supplementary heating or cooling may be controlled in order to maintain a desired temperature difference between the cameras 26, 28.

Although rollers 14 for rotating the pressure vessel 2 have been described, it will be appreciated that the pressure vessel 2 may be stationary and the cladding and inspection equipment 22, 26, 28 may be mounted on a rotating manipulator to achieve relative rotation. Similarly, the pressure vessel 2 may be moved along its axis 12 to effect relative axial movement, while the cladding and inspection equipment 22, 26, 28 maintains a fixed position along the axis.

Although the invention has been described with reference to a cylindrical pressure vessel 2, it will be appreciated that the component may be of any shape, and the invention may be applied to any component where a cladding layer is bonded to a substrate irrespective of its shape. Similarly, the relative movement between the component and the cladding and inspection equipment need not be rotational, but may be any relative movement as required to carry out the invention, such as linear or axial movement.

For example, the invention may be applied to a fuel rod, in which case the cladding and inspection equipment would be located around the external surface of the fuel rod.

The present invention is particularly useful in the inspection of components during a cladding process. Inspection can take place in real time and any defects can be identified and dealt with promptly. This avoids difficulties which can arise if repairs are effected after manufacture is complete. Such repairs can introduce additional stresses in the component and can create certification problems.

Nevertheless, a method in accordance with the present invention can be employed to inspect components after manufacture or in service. Specific areas of interest of the component can be inspected, and relative movement between the component and the inspection apparatus may not be necessary provided that the component undergoes a temperature change between the recording of the first and second images.

Although two cameras have been described, it will be appreciated that the first and second images could be recorded by the same camera. Similarly, there may be more than two cameras and/or more than two images may be recorded and compared.

Embodiments of the invention may make use of alternative imaging devices, for example, line scanners.

The invention claimed is:

1. A method of manufacturing a component, comprising:
applying a cladding layer to a substrate by a cladding process, thereby forming the component: and
inspecting the component comprising the cladding layer bonded to the substrate, the inspecting comprising:
recording a first image of an inspection portion of the cladding layer, the inspection portion having a pattern of markings;
causing or allowing a temperature change in the component;
recording a second image of the inspection portion; and
identifying a deformation of the pattern of markings on the inspection portion by reference to relative movement of the respective markings between the first image and the second image,
wherein the steps of applying the cladding layer and inspecting the compartment are applied concurrently to adjacent portions of the component.

2. The method according to claim 1, wherein the cladding layer and the substrate have different coefficients of thermal expansion.

3. The method according to claim 1, wherein the inspecting further comprises:
identifying regions of anomalous deformation of the pattern of markings on the inspection portion to identify locations of possible flaws in the component.

4. The method according to claim 1, wherein the inspecting further comprises:
applying the pattern of markings to the inspection portion.

5. The method according to claim 1, wherein the cladding process causes heating of the component to an elevated temperature, the temperature change in the component occurring as a result of cooling of the component from the elevated temperature.

6. The method according to claim 1, wherein the component is heated to the elevated temperature by heating means independently of the cladding process, the temperature change occurring as a result of the temperature elevation and/or subsequent cooling of the component from the elevated temperature.

7. The method according to claim 1, wherein
the component is substantially cylindrical or another shape having rotational symmetry,
the steps of applying the cladding layer and inspecting the component are performed respectively by cladding equipment and inspection equipment, and
there is relative movement between (i) the component and (ii) the inspection equipment and the cladding equipment, the relative movement being rotational movement about a rotational axis.

8. The method according to claim 7, wherein there is relative axial movement between (i) the component and (ii) the cladding equipment and the inspection equipment, whereby the cladding layer is formed in a helix on the component.

9. The method according to claim 1, wherein the component is a pressure vessel, and the cladding layer is applied to an internal surface of the pressure vessel.

10. A method for inspecting a component comprising a cladding layer bonded to a substrate, the method comprising:
recording a first image of an inspection portion of the cladding layer, the inspection portion having a pattern of markings;
causing or allowing a temperature change in the component;
recording a second image of the inspection portion; and
identifying a deformation of the pattern of markings on the inspection portion by reference to relative movement of the respective markings between the first image and the second image, wherein
the component is substantially cylindrical or another shape having rotational symmetry,
steps of applying the cladding layer and inspecting the component are performed respectively by cladding equipment and inspection equipment, and
there is relative movement between (i) the component and (ii) the inspection equipment and the cladding equipment, the relative movement being rotational movement about a rotational axis.

11. The method according to claim 10, wherein the cladding layer and the substrate have different coefficients of thermal expansion.

12. The method according to claim 10, wherein the step of inspecting the component further comprises:
identifying regions of anomalous deformation of the pattern of markings on the inspection portion to identify locations of possible flaws in the component.

13. The method according to claim 10, wherein the step of inspecting the component further comprises:
applying the pattern of markings to the inspection portion.

14. The method according to claim 10, wherein the component is a pressure vessel, and the cladding layer is applied to an internal surface of the pressure vessel.

15. The method according to claim 10, wherein there is relative axial movement between (i) the component and (ii) the cladding equipment and the inspection equipment, whereby the cladding layer is formed in a helix on the component.

* * * * *